(12) United States Patent
Mongeon

(10) Patent No.: US 6,318,367 B1
(45) Date of Patent: Nov. 20, 2001

(54) LARYNGEAL MASK ASSEMBLY

(75) Inventor: Douglas R. Mongeon, Orange Park Acres, CA (US)

(73) Assignee: Vital Signs, Inc., Totowa, NJ (US)

( * ) Notice: Subject to any disclaimer, the term of this patent is extended or adjusted under 35 U.S.C. 154(b) by 0 days.

(21) Appl. No.: 09/044,560

(22) Filed: Mar. 19, 1998

(51) Int. Cl.$^7$ ................................................ A61M 16/00
(52) U.S. Cl. .............................. 128/207.15; 128/207.14
(58) Field of Search .................. 128/200.26, 207.14, 128/207.15; 604/95.01, 95.04, 106, 107

(56) References Cited

U.S. PATENT DOCUMENTS

| | | | | |
|---|---|---|---|---|
| 3,543,751 | * | 12/1970 | Sheffer | 128/200.26 |
| 3,930,507 | * | 1/1976 | Berman | 128/200.26 |
| 4,509,514 | * | 4/1985 | Brain | 128/207.15 |
| 4,995,388 | | 2/1991 | Brain . | |
| 5,241,956 | | 9/1993 | Brain . | |
| 5,249,571 | | 10/1993 | Brain . | |
| 5,282,464 | | 2/1994 | Brain . | |
| 5,297,547 | | 3/1994 | Brain . | |
| 5,303,697 | | 4/1994 | Brain . | |
| 5,305,743 | | 4/1994 | Brain . | |
| 5,355,879 | | 10/1994 | Brain . | |
| 5,391,248 | | 2/1995 | Brain . | |
| 5,462,528 | * | 10/1995 | Roewer | 604/96 |
| 5,584,290 | | 12/1996 | Brain . | |
| 5,632,271 | | 5/1997 | Brain . | |
| 5,647,358 | * | 7/1997 | Vilasi | 128/207.14 |
| 5,682,880 | | 11/1997 | Brain . | |
| 5,915,383 | * | 6/1999 | Pagan | 128/207.15 |
| 6,050,264 | * | 4/2000 | Greenfield | 128/207.15 |

* cited by examiner

Primary Examiner—John G. Weiss
Assistant Examiner—Joseph F. Weiss, Jr.
(74) Attorney, Agent, or Firm—Kenyon & Kenyon

(57) ABSTRACT

An artificial airway device (also known as a Laryngeal Mask Assembly, "LMA," or Disposable Laryngeal Mask Assembly, "DLMA") used to facilitate lung ventilation in an unconscious patient and methods for using an artificial airway device. The device includes a curved but flexible airway tube and a hollow mask support at one end of the airway tube. The mask support includes a fairly rigid support base and a flexible, generally annular peripheral skirt which is attached to the support base. A distal tip of the mask support is narrowed and projects outwardly, thereby providing a nose portion which is used to easily locate the distal tip of the mask in the entrance into the esophagus. The skirt is capable of conforming to the space behind the larynx so as to form a seal around the circumference of the laryngeal inlet without penetrating into the interior of the larynx. The skirt surrounds a hollow interior space or lumen of the mask base into which the airway tube opens. During insertion of the LMA into the patient, the skirt is contracted, to make the LMA easier to insert into the patient's airway. The skirt of the mask can be selectively manipulated, e.g. expanded, to improve the sealing contact with the tissues around the circumference of the laryngeal inlet. The skirt, when expanded, and the support base form a "cup-like" shape, which enhances the stabilization and sealing of the mask in the airway.

49 Claims, 13 Drawing Sheets

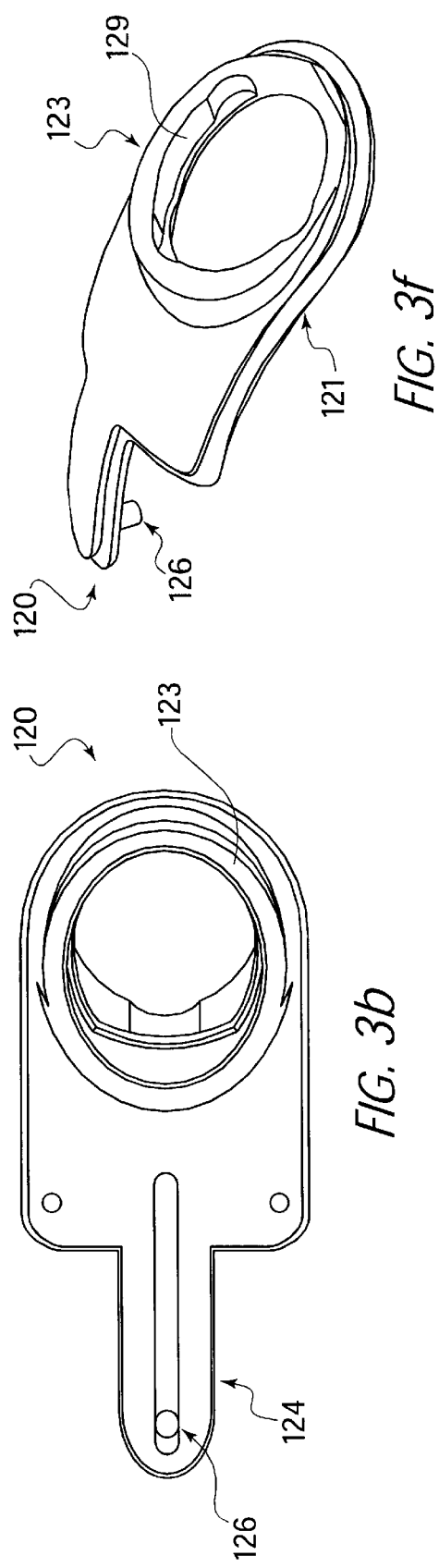
FIG. 3f
FIG. 3b
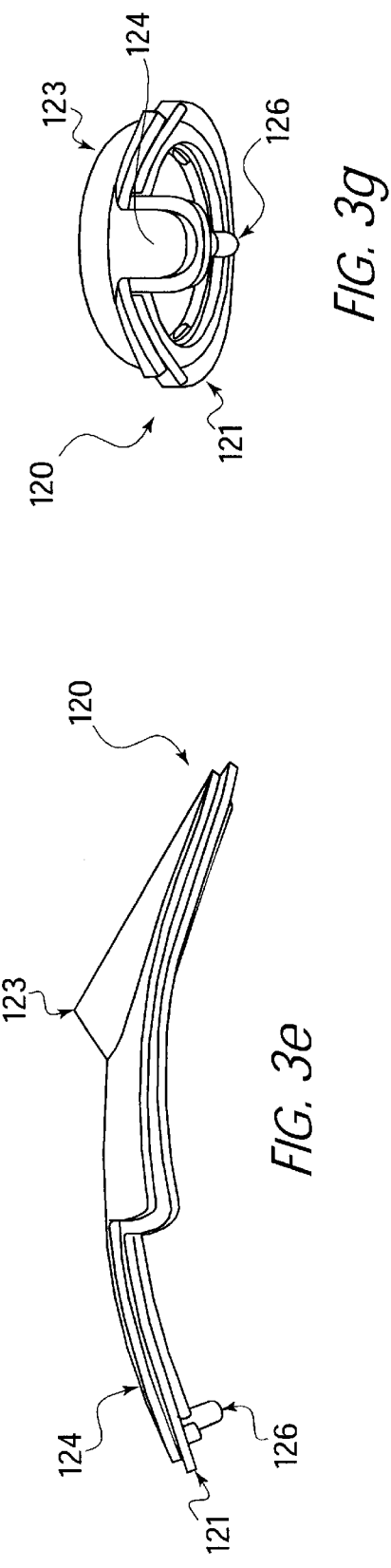
FIG. 3g
FIG. 3e

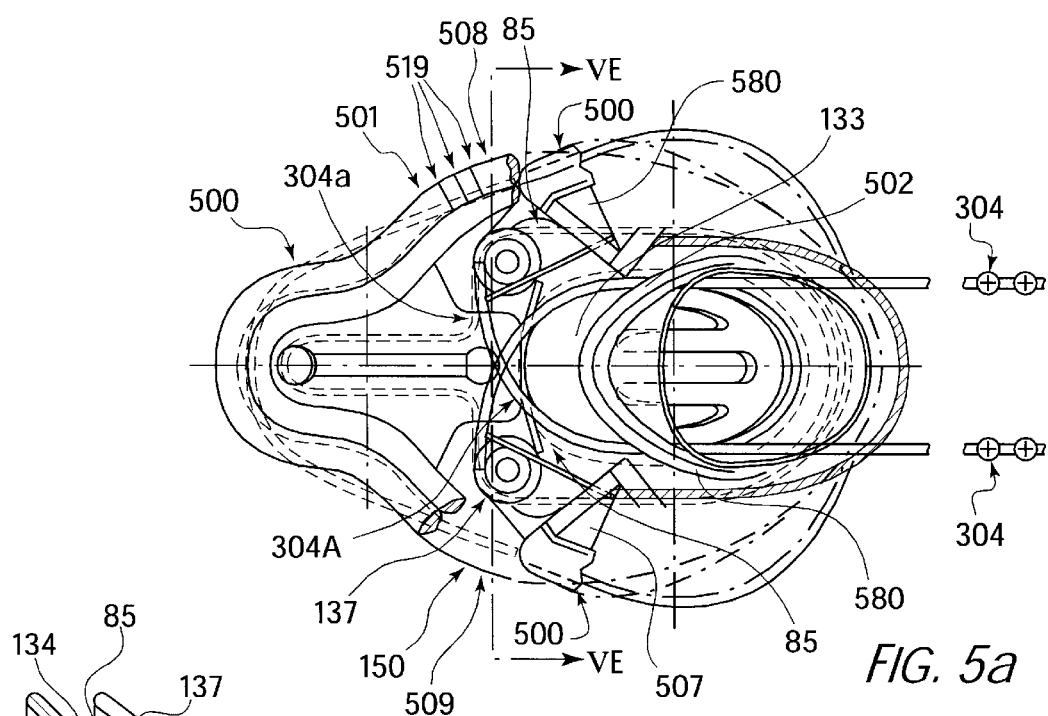
FIG. 5a
FIG. 5c
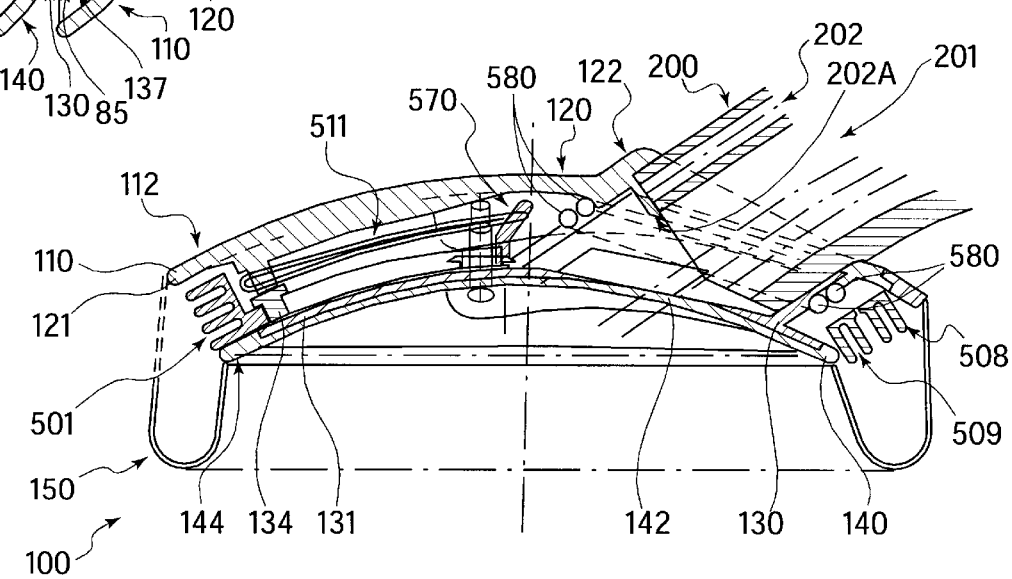
FIG. 4a

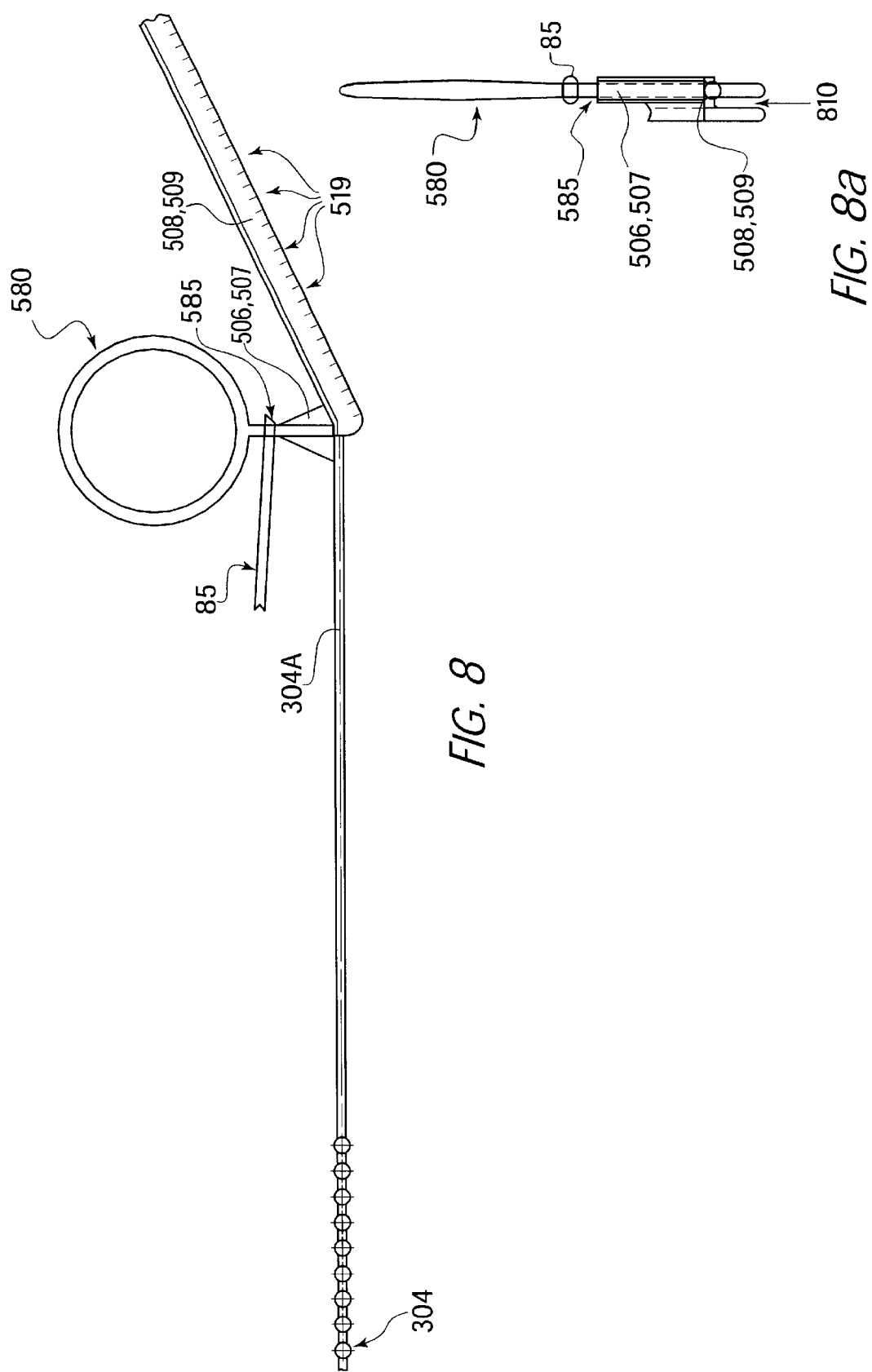

LARYNGEAL MASK ASSEMBLY

BACKGROUND OF THE INVENTION

1. Field of the Invention

The present invention relates to artificial airway devices used to facilitate lung ventilation in unconscious patients, and more specifically to devices designed for placement in the oropharynx of the patient in order to prevent airway obstruction an to permit either spontaneous or controlled ventilation.

2. Description of Related Art

To maintain open the airway of an unconscious patient under general anesthesia, it is common practice to use an endotracheal tube, which is a flexible tube of rubber or plastic which is inserted down through the trachea. Prior art endotracheal tubes frequently include an inflatable cuff around a distal end, which distal end is inserted into the trachea. The inflatable cuff is used to secure the endotracheal tube in place.

Typically, the endotracheal tube is introduced through nose and the larynx into the trachea or windpipe, and then the cuff is inflated through a small auxiliary tube in order to form a seal against the wall of the trachea. Introduction of the endotracheal tube into a patient is a skilled operation normally requiring use of a laryngoscope to guide the tube through the larynx, past the vocal cords and into the trachea. Intubation using an endotracheal tube is difficult or even impossible in some patients. Moreover, there is a significant risk of damage to soft tissues or to the larynx when using an endotracheal tube. Likewise, there is a risk of accidental, but highly undesirable, intubation of the esophagus or of the right or left main bronchus when using an endotracheal tube.

Alternatively, oro- or naso-pharyngeal airway devices may be used to maintain open the airway of a patient under general anesthesia. An oro- or naso-pharyngeal airway is a flexible tube extending from the mouth (oro-pharyngeal airway) or nose (naso-pharyngeal airway) into the patient's pharynx but not into the patient's larynx. An oro- or naso-pharyngeal airway is normally used in conjunction with a face mask over the patient's mouth and/or nose, unlike an endotracheal tube, which normally is not used with a mask. While preventing obstruction of the airway by the tongue, an oro- or naso-pharyngeal airway device cannot be used conveniently for controlled ventilation of the patient and does not prevent inhalation of extraneous matter (i.e., aspiration). For these and other reasons this type of device is less desirable in many applications.

Prior art artificial airways (see for example, U.S. Pat. Nos. 4,509,514; 4,995,388; 5,241,956; 5,249,571; 5,282,464; 5,297,547; 5,305,743; 5,355,879; 5,584,290; 5,632,271 and 5,682,880 to Archibald I. J. Brain—collectively, the "Brain patents") use a curved tube and a laryngeal mask portion at one end of the tube. The mask portion includes a flexible annular inflatable collar which surrounds a hollow interior space of the mask portion. The mask portion is pre-formed with a roughly elliptical shape which is purported to be capable of conforming to, and fitting within, the space behind the larynx to form a seal around the circumference of the laryngeal inlet without penetrating into the interior of the larynx. The curved tube opens into the mask portion and provides an airway with the axis of the tube substantially aligned with the length of the elliptical formation of the mask portion.

In the Brain patents, the curved tube opens into a lumen of the mask through an aperture which is provided with flexible cross-bars to prevent the aperture from being obstructed by the epiglottis, while permitting passage of a second smaller tube, such as an endotracheal or endobronchial tube, a suction catheter, or an inspection tube such as a fiber-optic broncho- or layrngoscope.

Even with the seal achieved by the inflatable collar in the Brain patents, there is a risk in some circumstances that if the contents of the stomach are regurgitated by the patient, the regurgitated material will travel from the esophagus and enter the bronchial tubes. The introduction of such foreign matter into the lungs, known as aspiration, is undesirable and should be avoided. Some of the Brain patents (e.g., U.S. Pat. Nos. 4,995,388; 5,241,956 and 5,632,271) attempt to solve this problem using gastric drainage features adjacent the inflatable collar.

Prior art artificial airway devices may include a drainage tube, such as those described above in certain of the Brain patents, having one end region arranged for insertion with the mask portion and the other end capable of being positioned below the patient foi extracting fluid from the area of the mask portion by siphonic action, or alternatively, the other end may be connected to an apparatus for extracting the fluid by suction. Typically, the drainage tube is of a smaller diameter than the airway tube so that the drainage tube may be accommodated within the airway tube, with the one end region opening into the lumen of the mask portion.

When the mask portion has an upstanding collar surrounding the lumen of the mask portion, the one end region of the drainage tube may be forked and adhered to the outside of the collar, with openings of the forked portions being arranged to extract fluid from the area around the exterior of the mask portion.

Alternatively, the one end region of the drainage tube may open into the esophagus when the mask portion has been inserted into the laryngeal space. For example, the one end region of the drainage tube may extend past the distal end of the mask portion so as to pass through the upper esophageal sphincter muscle. The drainage tube bifurcates at the distal end of the mask to provide fork portions lying adjacent respective lateral posterior surfaces of the flexible annular inflatable collar.

SUMMARY OF THE INVENTION

The present invention is an artificial airway device which is designed to overcome certain shortcomings which have been discovered with the use, in practice, of artificial airways of the type described in the Brain patents. The prior art laryngeal mask devices as shown in the Brain patents have a number of shortcomings, which make them ineffective or unusable in certain situations, and also result in such airways being expensive to use and therefore inappropriate for Emergency Medical Service (EMS) use. For example, the airway devices as shown in the Brain patents can have a tendency for the uninflated collar to pleat or fold during insertion, which results in incomplete expansion of the collar during inflation. Incomplete inflation results in leakage, which prevents effective use of the artificial airway. Furthermore, the inflatable collars often do not conform well to the airway, also resulting in leakage. In addition, it is often difficult for the individual inserting the artificial airway to determine whether the inflatable collar is completely inflated. In order to overcome these inflation and leakage problems, artificial airways with inflatable collars are often overinflated by the individual inserting the airway to pressures in the range of 20–30 cmH$_2$O, which pressures are sufficiently high that they can cause damage to the soft tissue against which the inflatable collar seals.

Another shortcoming of artificial airways using inflatable collars is that the mucous membranes which are in contact with the inflatable collar can become dried or irritated as the result of the contact pressure from the inflatable collar. Another difficulty with artificial airways using an inflatable collar is that it is often difficult for the individual inserting the airway to determine when the airway mask is properly in place over the larynx. This uncertainty of proper placement makes complete sealing more difficult, and also complicates insertion of the airway into the patient. Additionally, artificial airways with inflatable collars, because they must be completely inflated to properly seal, require a large number of sizes to accommodate the different sizes of airways of the patients to which they are administered.

Prior art artificial airways can also cause difficulties in ensuring that the airway does not accidentally enter the esophagus during insertion. Furthermore, these prior art artificial airways often do not have adequate mechanisms to anchor the mask in place after insertion. Finally, the prior art artificial airways often do not prevent gastric reflux, which may lead to aspiration, making them inappropriate for EMS use and make them only appropriate for controlled surgical use.

The present invention is an artificial airway device (also known as a Laryngeal Mask Assembly, "LMA," or Disposable Laryngeal Mask Assembly, "DLMA") used to facilitate lung ventilation in an unconscious patient and methods for using an artificial airway device, which overcome the shortcomings of prior art artificial airway devices. The device of the present invention includes a curved but flexible airway tube and a hollow mask support at one end of the airway tube. The mask support includes a fairly rigid support base which is, generally, pear shaped and a flexible, generally annular peripheral skirt which is attached to the support base. A distal tip of the mask support is narrowed and projects outwardly, thereby providing a nose portion which is used to easily locate the distal tip of the mask in the entrance into the esophagus. This nose portion helps ensure that the individual inserting the airway accurately positions the mask portion over the patient's laryngeal opening. The skirt is capable of conforming to the space behind the larynx so as to form a seal around the circumference of the laryngeal inlet without penetrating into the interior of the larynx. The skirt surrounds a hollow interior space or lumen of the mask base into which the airway tube opens. During insertion of the LMA into the patient, the skirt is contracted, to make the LMA easier to insert into the patient's airway. The skirt of the mask can be selectively manipulated, e.g. expanded, to improve the sealing contact with the tissues around the circumference of the laryngeal inlet. A biasing mechanism connected to the skirt automatically deploys the skirt into the expanded condition when a plunger mechanism is released by the operator. The skirt, when expanded, and the support base, form a "cup-like" shape, which enhances the stabilization and sealing of the mask in the airway. The skirt is preferably formed of a flexible sheet material which may be at least partially permeable to fluids, such as Coltran™ (manufactured by 3M and used in transdermal applications) or similar porous polyethylene or polymeric materials, thereby allowing the application of saline or other fluid substances to the tissue in contact with the skirt. This feature of the present invention prevents drying of the mucous membranes which are in contact with the skirt.

The shape of the deformable skirt of the mask ensures that it closely approximates the shape of the space between the laryngeal inlet and the walls of the lower part of the throat behind the laryngeal inlet. Because the skirt of the LMA of the present invention expands or "flowers" out uniformly with consistent pressure, only a few mask sizes are needed to accommodate a wide range of patient airway sizes, therefore reducing the number of sizes needed. This feature of the present invention also reduces costs, and makes the invention more amenable to EMS use, since fewer devices, and less storage space is needed by the EMS crew. In addition, the shape of the mask portion in its unexpanded or contracted position is such that it provide a good tactile indication when the mask portion is properly in place in the airway, thereby enhancing the ease and accuracy of insertion of the LMA in the patient. The mask portion includes a distal nose portion which seats in the entry to the esophagus during insertion, thereby providing an indication to the individual inserting the LMA that it is properly in place. Since the walls of tissue forming the back of the throat are relatively rigid, deformation of the mask skirt forces the skirt more tightly against the tissues surrounding the laryngeal inlet, resulting in an airtight seal while anchoring the mask in position. Moreover, because the skirt is caused to "cup" the laryngeal space, a more secure fit with greater integrity is obtained. In addition, because inflation is not used to expand the skirt, there is no risk of overinflation and the resultant potential damage to tissue, and pleating is also prevented.

The LMA of the present invention is designed to be easy and convenient to insert in the majority of patients. The LMA may also be inexpensively manufactured in quantity, thereby allowing it to be disposable. As a result, the LMA of the present invention may be more readily used in EMS or other non-hospital applications, as well as in surgical applications. When the distal tip of the mask portion reaches the upper end of the esophagus, a definite end-point can be felt by the individual inserting the LMA, indicating that the mask portion is correctly placed. The skirt is then manipulated by a control mechanism, passing through the airway tube and into the support base, to form the airtight seal. The mask portion does no, enter the larynx or trachea, so the risk of damage to these structures is avoided.

Likewise, the risk of accidental entry of the mask portion into the esophagus or one of the main bronchi is also avoided with use of the LMA of the present invention. Once in place, the LMA is generally used to allow the lungs to be ventilated by positive pressure. Alternatively, the patient may be permitted to breathe spontaneously after insertion of the LMA.

In addition, an inflatable bag and an attached tube may be inserted into the stomach of the patient via the tube and mask portion. The bag can be inflated and used as an anchor to secure the mask portion in position, and the attached tube may be used as a guide for inserting the mask portion into the patient's airway. The bag may also prevent gastric reflux from the stomach and aspiration into the patient's airway, making the LMA of the present invention more adaptable to emergency and EMS use, as well as adaptable to a larger variety of surgical applications than prior art artificial airways. As an alternative, a palate assist mechanism may be provided with the LMA of the present invention, to anchor the LMA in place using the patient's hard palate and tongue.

BRIEF DESCRIPTION OF THE DRAWINGS

FIG. 1a is a cross-sectional view of the airway tube, through line IA—IA of FIG. 1.

FIG. 3b shows a plan view of the underside of the upper insert of the embodiment of FIG. 2.

FIG. 3e is an elevation view of a side of the upper insert of the embodiment of FIG. 2.

FIG. 3f is a perspective view of the upper insert of the embodiment of FIG. 2.

FIG. 3g is an elevation view of an end of the upper insert.

FIGS. 4a and 4b show cross-sectional elevation views of the mask portion in the contracted and expanded positions, respectively, for the embodiment shown in FIG. 1.

FIGS. 5a and 5b show partial plan views of the manipulation ring for the skirt in the contracted and expanded positions, respectively, through lines IVA—IVA and IVB—IVB in FIGS. 5a and 5b, respectively.

FIG. 5c is a cross-sectional view of the support device, through line VC—VC of FIG. 5a.

FIG. 8 is a partial plan view of the expansion ring with an attached beaded chain.

FIG. 8a is an elevation view of the control ring support of the expansion ring.

DESCRIPTION OF THE PREFERRED EMBODIMENTS

Figure 1:
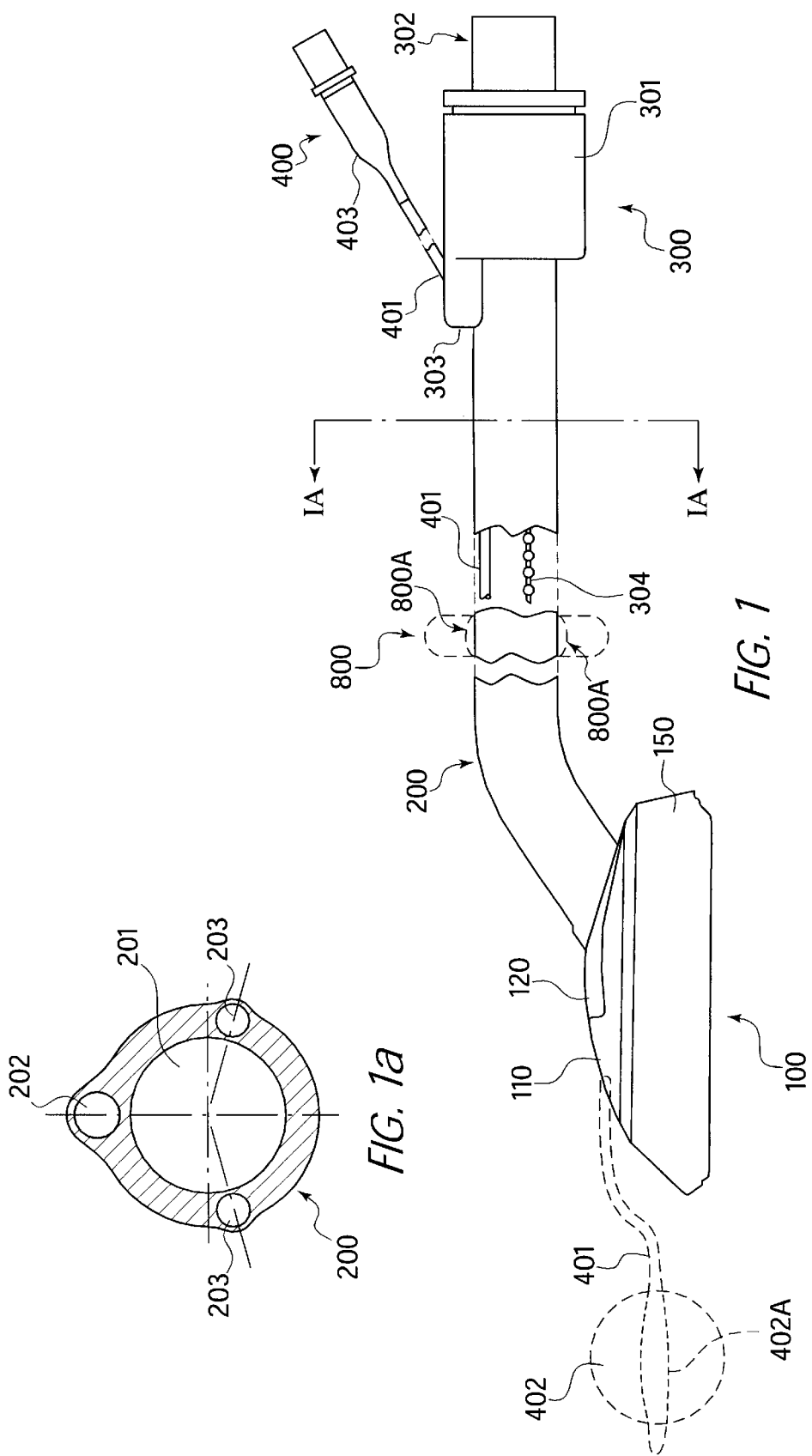
FIG. 1 is a partially broken away elevation view of one embodiment of the laryngeal mask assembly of the present invention.

FIG. 1 is a partially broken-away elevation view of one embodiment of the laryngeal mask assembly (LMA) or disposable laryngeal mask assembly (DLMA) of the present invention. In the embodiment of FIG. 1, the mask portion 100 is connected to a partially curved away tube 200 which includes a plunger cap 300. An anchor balloon unit or fluid supply unit 400 is an optional feature for certain embodiments of the present invention.

In the embodiment shown in FIG. 1, the mask portion 100 includes an upper support plate 110 and an upper insert 120. The upper insert 120 is attached to and fits into an opening in the upper support plate 110. A flexible skirt 150, formed of a thin, flexible, biologically-neutral material which may be at least partially permeable to fluids, such as Coltran™ (manufactured by 3M and used in transdermal applications) or similar porous polyethylene or polymeric materials, is attached to and projects from the upper support plate 110. The use of a partially permeable material allows the application of saline or other fluids to the tissue which is in contact with the flexible skirt when the LMA of the present invention is deployed and expanded in place in the patient's P airway, thereby allowing mucous membranes to be irrigated and/or drugs to be administered to that tissue. The permeability of such a material to gases, such as air, oxygen or anesthesia, is sufficiently slow so that there is no appreciable leakage of the delivered gas through the skirt 150. The skirt 150 is also attached to a lower support plate 140. The skirt 150 can be expanded or contracted by the individual responsible for inserting the LMA into the patient P by operating the plunger cap 300. The plunger cap 300 controls the operation of an expansion ring 500 within the skirt 150, thereby controlling expansion and contraction of the mask portion 100.

The airway tube 200 is fixed to the mask portion 100. In the preferred embodiment of FIG. 1, the airway tube 200 is made of a material which is sufficiently flexible to permit it to deform so as to fit down the patient's airway (see FIG. 10), but is also sufficiently stiff to permit the airway tube 200 and the mask portion 100 to be accurately positioned manually in the patient P. Polyvinyl chloride (PVC), or any other known inexpensive, durable and partially flexible material may be used as the material from which the airway tube 200 is made.

Figure 10:
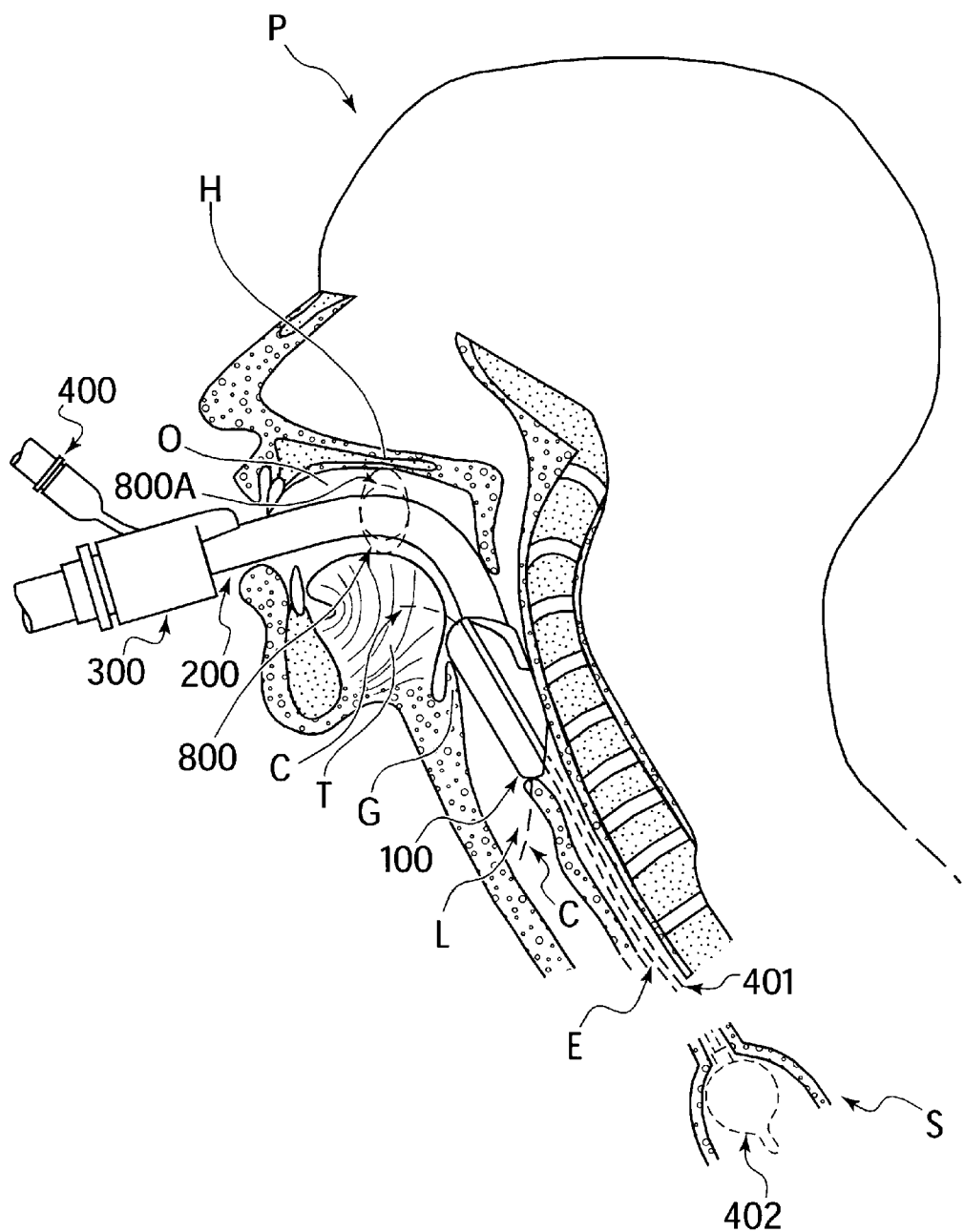
FIG. 10 is a partially cross-sectional view of the laryngeal mask assembly of the present invention, as inserted in the airway of a patient.

The airway tube 200 includes a cent al bore 201 through which various fluids (e.g., anesthesia, oxygen, air) can be administered to the patient, if and when desired. In addition, the airway tube 200 includes a small conduit 202 in the tube wall. The conduit 202 may be used to pass a balloon tube 401 and a balloon 402 into the patient's P esophagus E and stomach S (FIG. 10). Alternatively, conduit 202 may be used to transmit a fluid to inflate a palate assist mechanism 800. The airway tube 200 in the embodiment of FIG. 1 also includes a pair of conduits 203 formed in the wall of tube 200. These conduits carry, in the embodiment of FIG. 1, beaded chains 304 which are attached to the inner end of the cylinder 302 of the plunger cap 300. Although beaded chains 304 are used in the preferred embodiment, it is to be understood that any elongated flexible member, such as wires, cords, etc., may be used to contract and expand the skirt 150 in the manner described below. A balloon tube access port 303 is formed as part of an outer sleeve 301 of the plunger cap 300, and the balloon tube access port 303 permits the balloon 402 and balloon tube 401 to be inserted into the small conduit 202.

The cylinder 302 is arranged to move within the outer sleeve 301 of the plunger cap 300. Ends of the beaded chains 304 are connected to and movable with the cylinder 302, while the other ends of beaded chains 304 are preferably integral with the expansion ring 500 used to control the deployment of the skirt 150.

In the embodiment of FIG. 1, the anchor balloon 400 is an optional feature, and is therefore shown in dashed lines. When used with the LMA of the present invention, anchor balloon 402 is attached to a balloon tube 401 which passes through the mask portion 100 (as described below with reference to FIG. 11), through the airway tube 200 (via small conduit 202) and through a portion of the plunger cap 300 to a connector 403. The connector 403 is selectively connected to any source of moderate fluid pressure, such that pressurized fluid (such as air or water) is supplied, via tube 401, to the balloon 402. When the pressurized fluid is supplied to the balloon 402, the balloon 402 expands to take the configuration shown with reference numeral 402 in FIGS. 1 and 10. In the absence of pressurized fluid, the balloon is deflated to the outline shown with reference numeral 402A. The balloon 402 is deflated when it is passed through conduit 202.

In one method of inserting the LMA of the present invention into a patient, the deflated balloon 402A and the balloon tube 401 are inserted through the airway tube 200 and the mask 100 so that the LMA may slide along the balloon tube 401. The balloon tube 401 and deflated balloon 402A may thereafter be inserted down the patient's P esophagus E and into the patient's P stomach S (see FIG. 10). The balloon 402 is then inflated through the connector 400 (and the balloon tube 401) so that the inflated balloon 402 is anchored in the Patient's P stomach S and the inflated balloon 402 blocks gastric reflux from exiting into the esophagus. The LMA of the present invention is thereafter slid down the balloon tube 401 until it is in place in the patient's P airway, directly above the patient's P larynx L. The balloon tube 401 therefore assists in guiding the LMA into the patient's P airway, while the expanded balloon 402 assists in retaining the mask 100 in place within the patient P. As an alternative method of anchoring the LMA of the present invention in place, the mask portion 100 is first inserted in place in a patient P. The balloon 402 and the balloon tube 401 may then be inserted into the patient P, through the airway tube 200 and the mask 100, into the patient's P stomach S. The balloon 402 is then inflated through the connector 400 (and tie balloon tube 401) so that the inflated balloon can act as an anchor to assist in retaining the mask 100 in place within the patient P and preventing gastric reflux.

An alternative configuration for anchoring the LMA of the present invention in place is also shown in FIGS. 1 and 10. A palate assist 800, which is in the form of a fluid-expandable pillow, is mounted on the shaft of the airway tube 200, in a location on the tube 200 where it is adjacent the hard palate H and the tongue T of the patient when the LMA of the present invention is in place over the larynx L. During insertion of the LMA of the present invention into the airway of the patient P, the palate assist 800 is in a contracted position 800A. An opening (not shown) through the wall of airway tube 200 leads from the conduit 202 to the interior of the palate assist 800. Once the LMA of the present invention is in place, fluid may be applied to connector 400, thereby expanding the palate assist 800 to the condition shown with reference numeral 800 in FIGS. 1 and 10. The palate assist 800, in the expanded condition, contacts the hard palate H and tongue T of the patient P, thereby anchoring the LMA of the present invention in place within the airway of the patient P. In the embodiment of the present invention which uses a palate assist, the end of the conduit 202 near the mask portion 100 is closed off by a shelf 202A (FIGS. 4a and 5a), so that fluid applied to conduit 202 travels only to the interior of palate assist 800.

Figure 2:
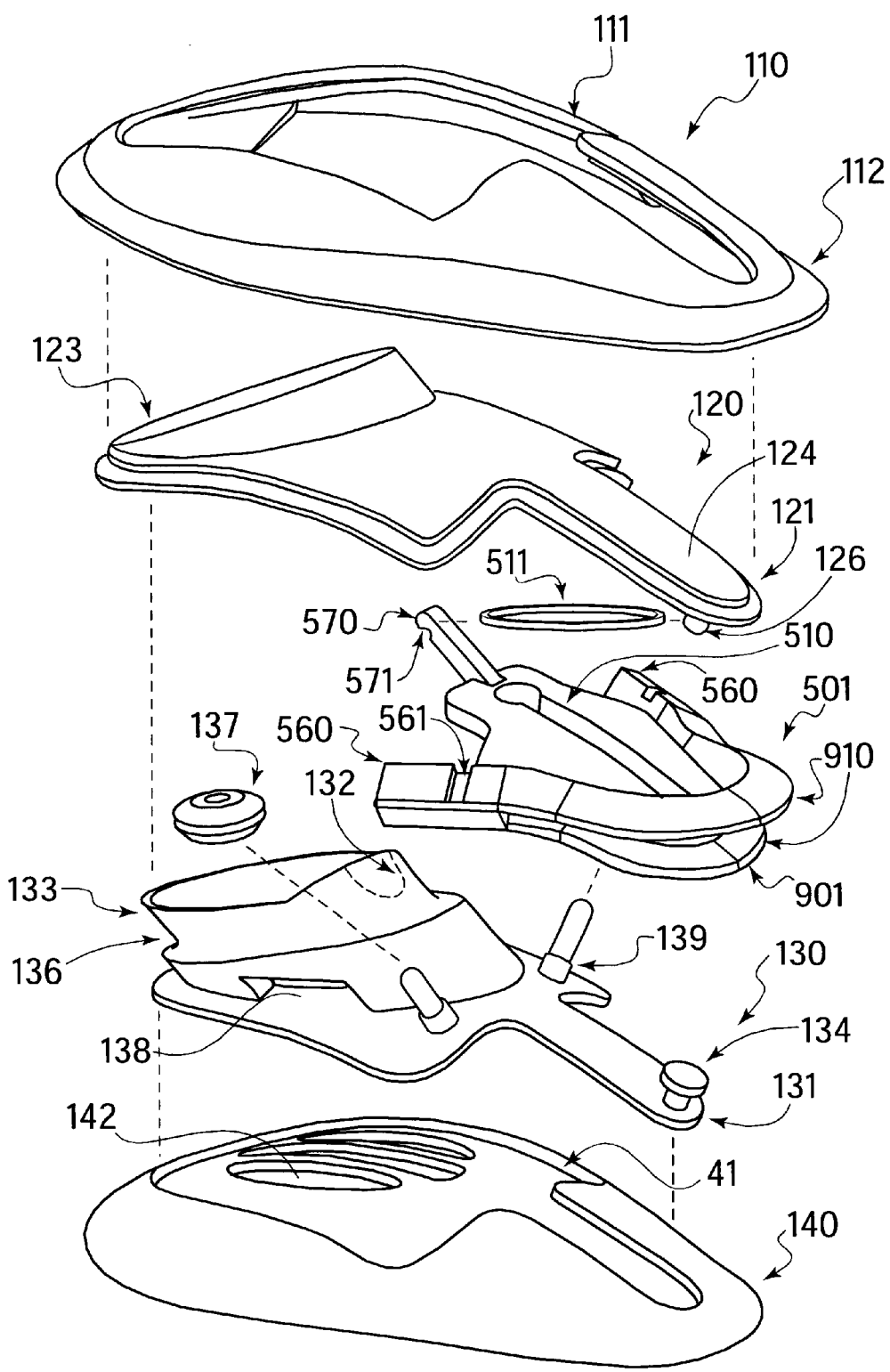
FIG. 2 is an exploded perspective view of one embodiment of the mask support of the laryngeal mask.
Figure 4B:
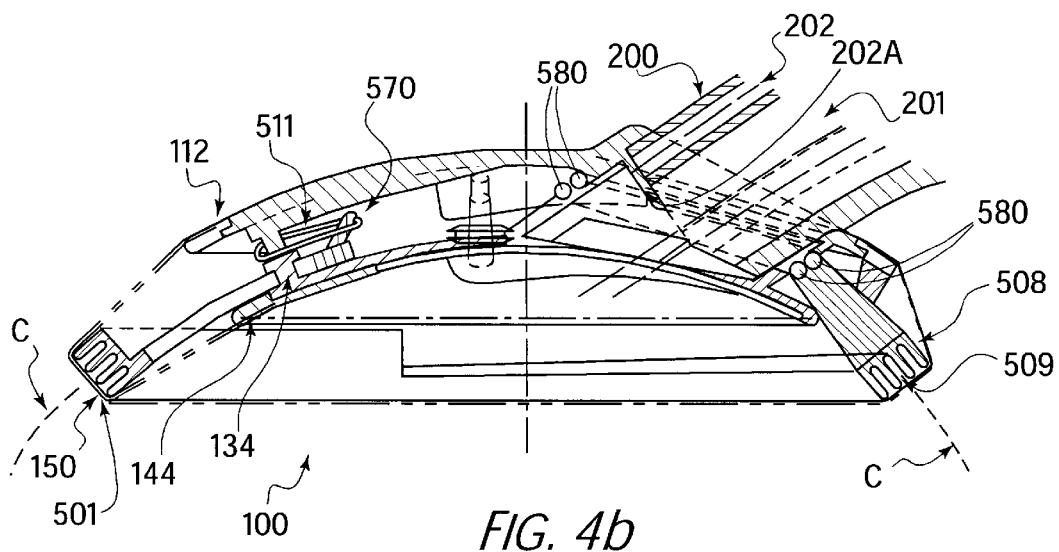

Referring now to FIG. 2, there is shown an exploded perspective view of the support structure for one embodiment of the mask portion 100. In particular, an upper support plate 110 is a generally curved component which is, typically, formed of a flexible plastic or rubber material. A shallow recess 112 is formed around the periphery of the plate 110. The thin membrane which forms skirt 150 is affixed to the recess 112 (see FIGS. 4a and 4b) by any known attachment method, which may include the use of an adhesive, or a hot seal. The skirt 150 is preferably formed of two or more pieces of material which are adhesively connected or hot sealed together to form the three-dimensional skirt configuration as shown in FIGS. 1 and 4b. The upper support plate 110 includes an opening 111 in an upper surface to receive the upper insert 120.

The upper insert 120 is preferably formed of a fairly rigid plastic or rubber material. The upper support plate 110 and upper insert 120 are curved in a generally clamshell shape. The upper insert 120 fits securely in and engages the opening 111 in the upper support plate 110. The upper surface of upper insert 120 passes through the opening 111 in upper support plate 110 and fits together so that the upper surfaces of upper insert 120 and upper support plate 110 are flush. A shelf or shoulder 121 is formed around the edge of upper insert 120 and engages a similar counterpart shoulder formed underneath the opening 111 on the inner surface of upper support plate 110. An elongated nose 124 extends from one end of the upper insert 120. A spring post 126 is located on an underside of elongated nose 124. A spring 511 is attached at one end to the spring post 126.

A generally partially cylindrical port 123 extends upwardly from the top surface, and downwardly from the bottom surface, of the upper insert 120. The lower end of port 123 encircles the upper end of a port 133 on the lower insert 130, and is angled downwardly. The upper end of the cylindrical port 123 includes a slot 129 into which the end of the airway tube 200 fits.

A lower insert 130 which may be formed of a fairly rigid plastic or rubber material fits together with upper insert 120, and is also shaped to comfort to the curvature of a lower support plate 140 and to fit within a recess 141 in lower support plate 140. The lower insert 130 includes an elongated nose 131.

A substantially cylindrical port 133 extends upwardly from the upper surface of the lower insert 130. The port 133 is inserted into port 123 in the upper insert 120. A radiused portion or inset portion 136 is formed in the outer surface of port 133. The radiused portion 136 is angled downwardly. This radiused portion 136, together with the bottom of the port 123, form a channel in which control rings 580 (FIG. 8) slide. A slot 138 is formed on both sides of the port 133 to allow passage of a non-beaded portion 304A of beaded chain 304.

Figure 3A:
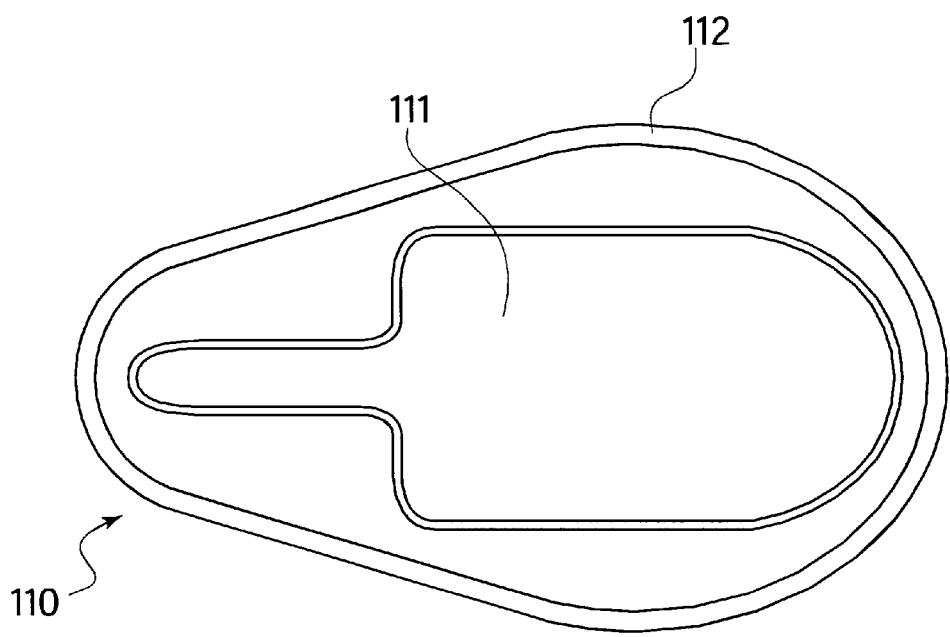
FIG. 3a shows a plan view of the upper support plate of the embodiment of FIG. 2.
Figure 3D:
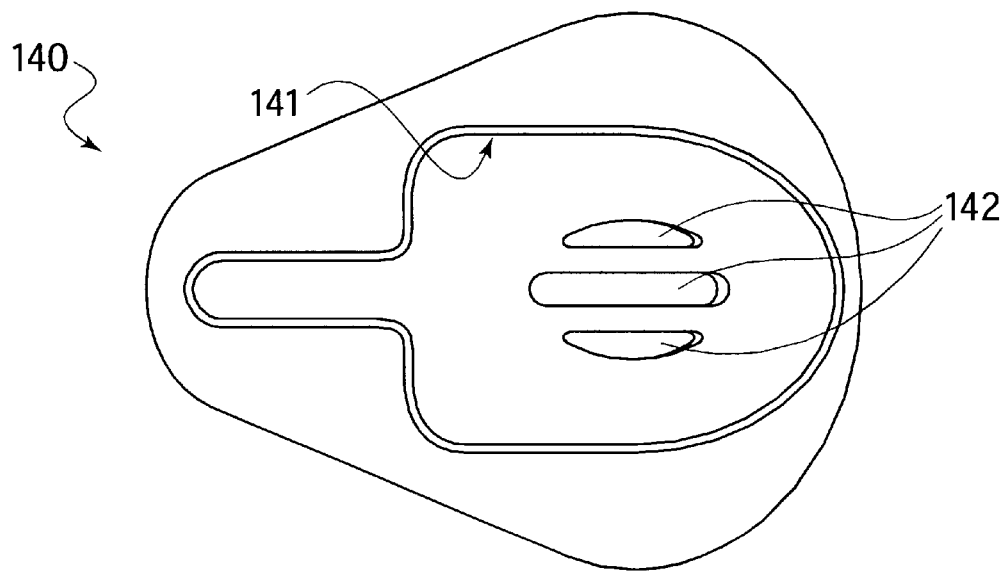
FIG. 3d shows a plan view of the lower support plate of the embodiment of FIG. 2.
Figure 3I:
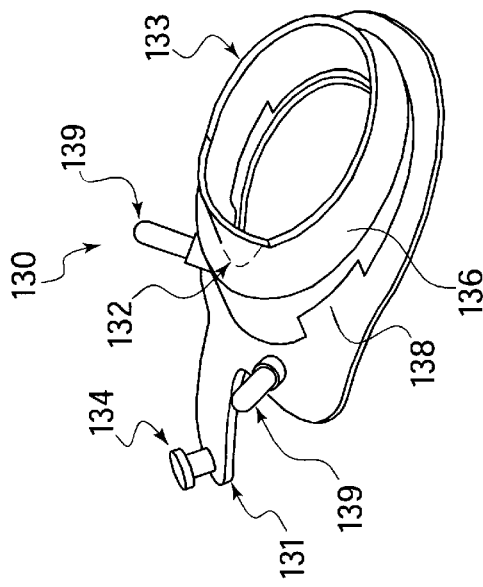
FIG. 3i is a perspective view of the lower insert of the embodiment of FIG. 2.
Figure 3J:
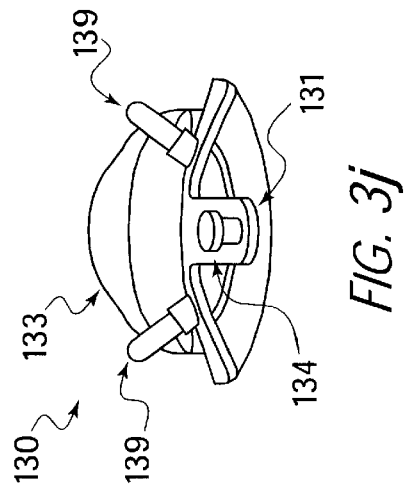
FIG. 3j is an elevation view of ar end of the lower insert of the embodiment of FIG. 2.
Figure 3C:
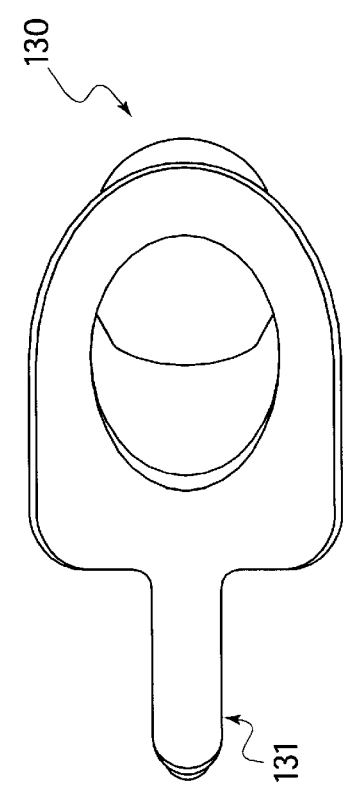
FIG. 3c shows a plan view of the underside of the lower insert of the embodiment of FIG. 2.
Figure 3H:
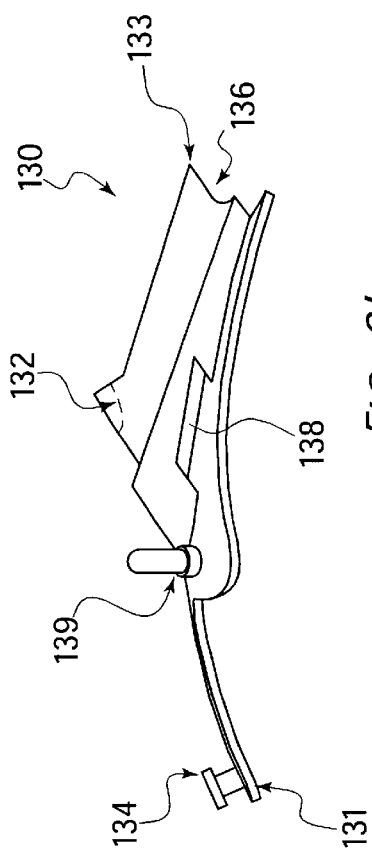
FIG. 3h is an elevation view of a side of the lower insert of the embodiment of FIG. 2.

The front of the port 133 may includes an aperture or slot 132 (shown in dashed lines in FIGS. 2, 3h and 3i). This slot 132 allows the passage 128 for balloon tube 401 to pass through the lower insert 130, in the embodiment shown in FIG. 11.

A pair of pulleys 137 are disposed at the corners of the lower insert 130, and are mounted on the lower insert for rotation on a pair of posts 139. The pulleys are used to guide and control the expansion and contraction of the expansion ring 500, which expands and contracts the skirt 150. Resilient retainers 85 (shown in dashed outline) such as rubber bands, have one end looped around posts 139 and extend around the exterior of port 133. The retainers 85 are used in the LMA of ale present invention to control and bias the position of expansion ring 500 and skirt 150. The opposite end of resilient retainers 85 are looped around the stems 585 of supports 506 and 507, thereby biasing the skirt 150 into the expanded position shown in FIGS. 4b and 5b. The elastic retainers 85 also extend around the outer surface of port 133.

Located between upper and lower inserts 120, 130 is a ring tip 501. The ring tip 501 is preferably integrally formed with the ring arms 508 and 509 as part of a composite expansion ring 500, although as shown in FIG. 2, the ring tip 501 can include ends 560 with bores 561 for receiving ends of the ring arms 508 and 509.

The ring tip 501 includes an arcuate peripheral nose piece 901. The nose piece 901 has the arcuate (or curved) configuration to assist in positioning the mask portion 100 in the laryngeal space in a patient without causing a substantial amount of trauma, and assists in seating the mask portion 100 in place by entering into the entry to the esophagus E. The curved configuration also smoothly conforms to the shape of the other portions of the mask assembly.

The ring tip 501 is bowed slightly upwardly to conform to the clamshell shape of the mask portion elements shown in FIG. 2. The periphery of the ring tip 501 includes channels 910 which cooperate with the groove 810 in the control ring support 506, 507 and the ring arms 508, 509 shown in FIG. 8.

A slot 510 in ring tip 501 fits around post 134 on lower insert 130. This slot 510, as it interacts with post 134, controls the movement of the ring tip 501, and ensures that the ring tip is deployed only radially outwardly, and does not move laterally, thereby ensuring that the ring tip 501 remains in place in the entry to the esophagus E during deployment.

A spring 511, preferably in the form of a rubber band, is connected at one end to spring post 126 on upper insert 120, and spring 511 is connected at the other end to spring post 570, including slot 571, on ring tip 501. The spring 511 is used to bias the ring tip 501 outwardly, to assist in the expansion or deployment of the ring tip 501 and expansion ring 500.

A lower support plate 140, which may be formed of formed of a flexible plastic or rubber material has a hollow curved configuration of a generally clamshell shape. A recess 141 is formed in the upper surface of lower support plate 140. The recess 141 receives and secures the lower insert 130. The lower support plate also includes a shallow recess 144 (see FIGS. 4a and 4b) which is formed around the periphery of the lower plate 150. The thin membrane which forms skirt 150 is affixed to the recess 144 by any known attachment method, including the use of an adhesive, or by a hot seal.

Referring now to FIGS. 3a through 3j, there are shown various views of the components in FIG. 2. In FIG. 3a, there is shown a plan view of the upper support plate 110. The recess 111 is shown formed in the upper surface of upper support plate 110. The shoulder 112 is disposed around the perimeter of plate 110.

Figure 11:
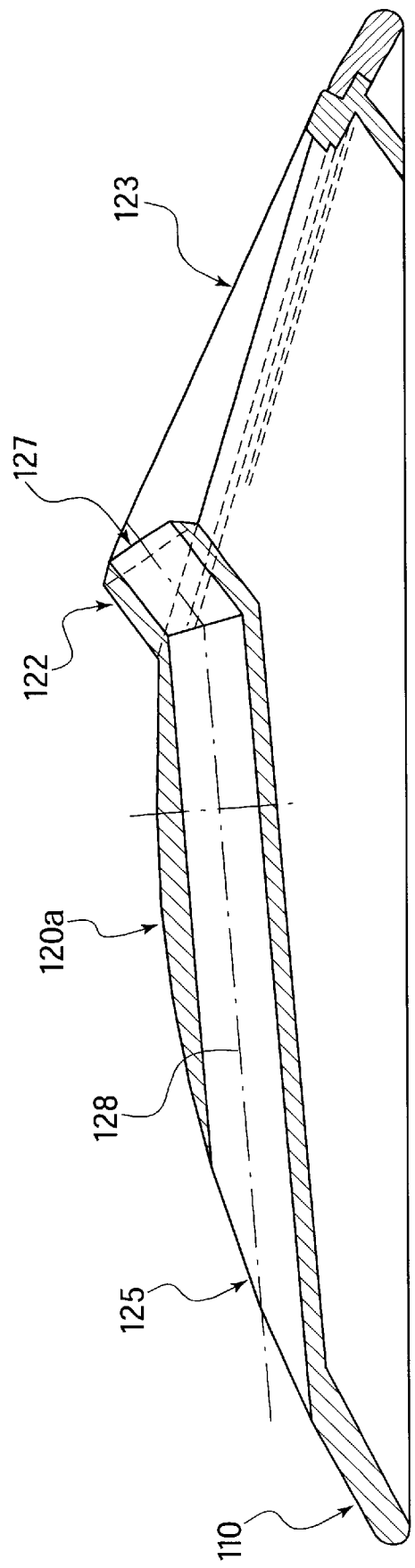
FIG. 11 is a cross-sectional, partial assembly, elevation view of a second embodiment of the upper support plate and upper insert of the present invention.

FIG. 3b is a plan view of the underside of the upper insert 120, which includes the elongated nose 124, upon which spring post 126 is mounted. The upper insert 120 is received and is held in the recess 111 of the upper support plate 110. As shown in FIG. 11, in one embodiment, the elongated nose 124 may include an aperture 125 passing through elongated nose 124 which communicates with aperture 127, via passage 128, in the port 122 in order to receive the balloon 402 and the balloon tube 401, when those components are used with the LMA of the present invention. The aperture 125, when used, allows the balloon 402 and balloon tube 401 to pass from the conduit 202, through the mask portion 100 and to the exterior of the mask portion 100.

The shoulder 121 interacts with the inner surface of upper support plate 110 so that the upper surface of upper insert 120 and the upper surface of upper support plate 110 are flush.

Referring to FIG. 3d, the lower support plate 140 has a plurality of apertures 142 disposed in and through the surface of the lower support plate 140. These apertures 142 are used to pass air, oxygen, anesthesia or other fluid from the airway tube 200 through the mask portion 100 and into the patient's P larynx L. A recess 141 is formed in the upper surface of lower support plate 140 to receive the lower insert 130. The recess 141 may be spade-shaped and surrounds the apertures 142.

Referring now to FIG. 3c, there is shown a plan view of the underside of the lower insert 130. The nose 131 extends outwardly and is adapted to be inserted into the extended portion of recess 141 in lower support plate 140.

The posts 139 are shown integrally formed on the upper surface of lower insert 130. These posts 139 have looped around them one end of the resilient retainers 85, which are used to bias and control the control rings 580 which are in turn used to expand and contract the skirt 150. The posts 139 also have mounted upon them, for rotary movement, the pulleys 137. The retainers 85 may be in the form of elastic or rubber bands and are located between the upper and lower inserts 120, 130 and encircle the port 133 so that the retainers bias the skirt into the expanded position shown in FIGS. 4b and 5b.

The port 133 extends upwardly from the surface of lower insert 130 and includes the radiused portion 136. In addition, a post 134 is provided to control movement of the ring tip 501.

Figure 5B:
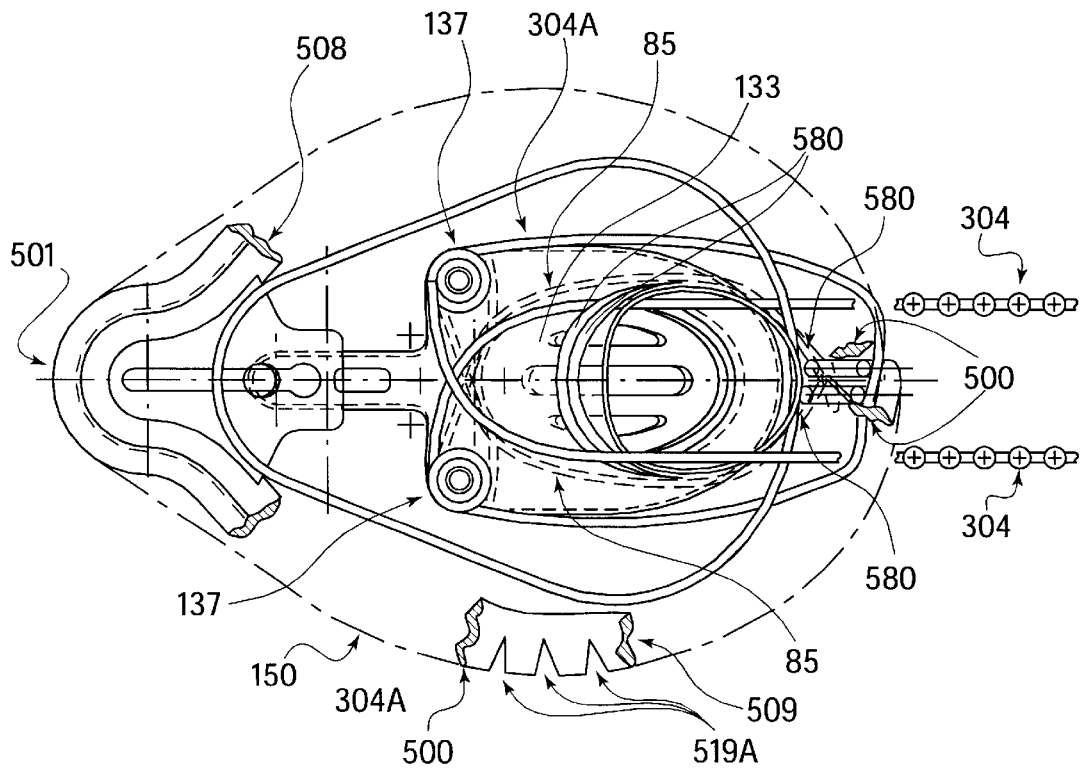

Referring now to FIGS. 4a and 4b, there are shown plan views of an assembled mask portion 100, in contracted and expanded positions, respectively. In FIGS. 5a, 5b and 5c, the upper insert 120 is shown mounted in the upper support plate 110 which is mounted above lower support plate 140. The lower insert 130 is mounted beneath the upper support plate 110 in lower support plate 140. A non-beaded portion 304A of the beaded chains 304 extends through slots 138, as may be seen in FIG. 5a.

Referring concurrently to FIGS. 4a, 4b, 5a and 5b, there is shown the expansion ring 500 (which is partially broken away for clarity) and the control components used to expand and contract the expansion ring 500. The expansion ring 500, which includes ring tip 501 and ring arms 508, 509, is disposed between plates 120 and 130 when the mask portion 100 is assembled (see FIGS. 4a and 4b). In particular, FIGS. 4a and 5a show the expansion ring 500 in the closed or contracted position. In this condition, the skirt 150 is deployed limply around the periphery of the mask portion 100. Conversely, FIGS. 4b and 5b show the expansion ring 500 in the open or fully deployed or expanded position. In this condition, the skirt 150 is deployed around the mask portion 100 to form the seal in the space above the larynx L (FIG. 10).

As shown in FIGS. 5a, 5b and 8, the ends of the expansion ring 500, i.e., the ends of ring arms 508, 509, are preferably integrally molded with the non-beaded portions 304A of beaded chains 304. Beaded chain 304 passes through conduits 203 in airway tube 200, while non-beaded portion 304A passes through slot 138, over pulleys 137 and around port 133. The opposite ends of the beaded chains 304 are connected to the inner end of cylinder 302 of plunger cap 300. Thus, when the cylinder 302 is pulled (or otherwise positioned) axially outwardly relative to the plunger cap 300, chains 304 pull the ends of expansion ring 500 into a relatively tightly curled or coiled configuration as shown in FIGS. 5a and 5b. In this configuration, the flaccid skirt 150 hangs limply from the mask portion 100. The contracted or coiled configuration of the expansion ring 500 is used during insertion of the mask portion 100 into the patient's P airway.

Conversely, when the cylinder 302 is released or otherwise moved axially inwardly, the resilient retainers 85 pull on stems 585 of expansion arms 508, 509, and thus pull the ends of the expansion ring 500 to the position shown in FIG. 4b and 5b, at the same time pulling the beaded chains 304 and cylinder 302 axially inwardly and sliding the control rings 580 around the port 133 in the radiused portion 136. The expansion ring 500 is relaxed upon release of the cylinder 302, so that it expands relative to the tightly coiled condition in FIGS. 4a and 5a. When the ring 500 expands (as shown in FIGS. 4b and 5b) the skirt 150 is forced outwardly in a uniform manner around the entire periphery of the expansion ring 500. As is seen in FIG. 4b, the expanded skirt 150 is forced both radially outwardly and axially outwardly relative to the mask support 100. This radially and axially outward motion creates a "cup-like" configuration C of the skirt 150 relative to the mask portion 100, which aids in sealing the mask portion 100 against the laryngeal opening.

In the assembled device, the expansion ring 500 is mounted between the inserts 120 and 130 shown in FIG. 2. In particular, the expansion ring 500 fits over the port 133 and each of the control rings 580 are looped over the port 133 in radiused portion 136 so that the control rings slide circumferentially around radiused portion 136. Because radiused portion 136, and the bottom of port 123, are angled downwardly, the expansion ring 500 expands axially outwardly (i.e., downwardly) and radially outwardly, and contracts radially inwardly and radially inwardly. As a result, during expansion, the skirt 150 forms a cup-like shape C. This action and configuration provide a mask portion 100 which covers the laryngeal space L and, as well, forms a secure seal of the laryngeal space L.

As is seen in FIGS. 4a and 5a, the ring 500 is contracted when the cylinder 302 is pulled axially outwardly. That is, the beaded chain 304 and non-beaded portions 304A pull on the ring arms 508, 509, which causes the control rings 580 to slide around port 133, until the ring arms 508, 509 assume the position shown in FIGS. 4a and 5a. The control ring supports 506 and 507 are integrally formed with the flexible ring arms 508 and 509, the ring arms 508, 509 being contracted within the perimeter of the mask support 100. Thus in the contracted position, the skirt 150 remains limp and flaccid (FIG. 4a), so that the overall mask portion 100 has a minimal radial dimension and is easily inserted down the patient's P oral cavity O and into the area above the laryngeal space L.

The resilient retainers 85 are looped around the stems 585 of supports 506 and 507 below the control rings 580, and are also looped around and anchored to the posts 139. The resilient retainers 85 provide tension to the supports 506, 507, thereby biasing the supports 506, 507 (and as a result the expansion ring 500 which is integral with the supports 506, 507) into the expanded or deployed position shown in FIGS. 4b and 5b.

A post 134 fits in a slot 510 in ring tip 501 to thereby control the amount of radially outward movement of ring tip, and also to prevent lateral movement of ring tip 501. This feature assists in ensuring that ring tip 501 stays properly situated in the esophageal opening during deployment of the skirt 150, thereby ensuring that the placement of the skirt 150 remains proper on deployment.

A spring post 126 on upper insert, and a spring post 570 on ring tip 501, each have mounted on them one end of a spring 511. A slot 571 on spring post 570 may assist in retaining spring 511 on spring post 570. The spring 511 is preferably a rubber band, which biases the ring tip 501 into the expanded position shown in FIGS. 4b and 5b. The spring 511 therefore assists in expanding the expansion ring 500 into the deployed or expanded position.

When the cylinder 302 is released by the operator, the resilient retainers 85 pull the non-beaded sections 304A axially inwardly. The resilient retainers 85 retract and pull the control ring supports 506 and 507 toward the rear of the port 133 (as shown in FIGS. 4b and 5b), so that the expansion ring 500, guided by the control rings 580, follows the downward path of the radiused portion 136.

In a preferred embodiment, the expansion ring 500 is composed of two ring arms 508 and 509 formed integrally with a ring tip 501, control rings 580, and control ring supports 506, 507, which are also formed integrally with non-beaded portions 304A and beaded radius 304, thereby allowing the LMA of the present invention to be more easily assembled and less expensive to manufacture. Alternatively, the ring arms 508 and 509 could be snap-fit or otherwise attached into bores 561 in a separate ring tip 501 (see FIG. 2), to permit assembly of various sizes of expansion rings 500 while requiring a smaller inventory of fixed-size components.

Figure 6A:
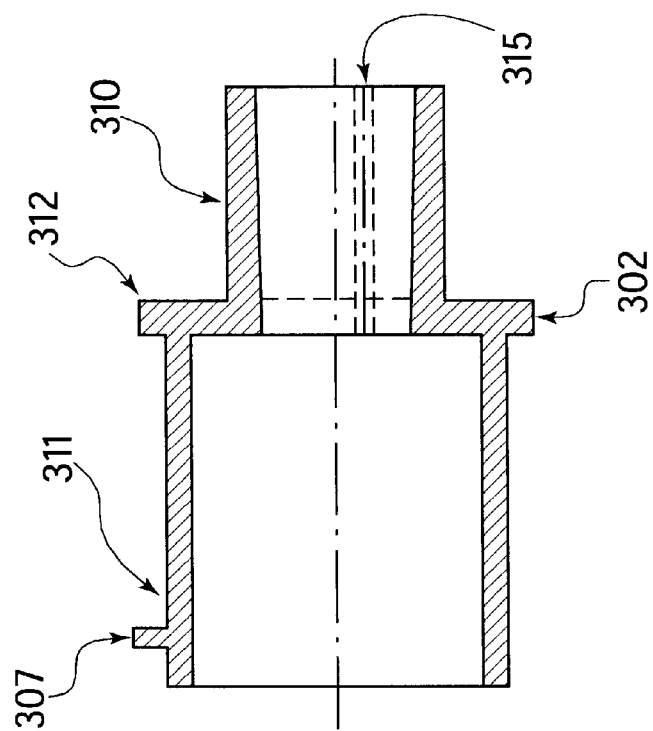
FIG. 6a is a cross-sectional view of the cylinder, through line VIA—VIA of FIG. 6.
Figure 6:
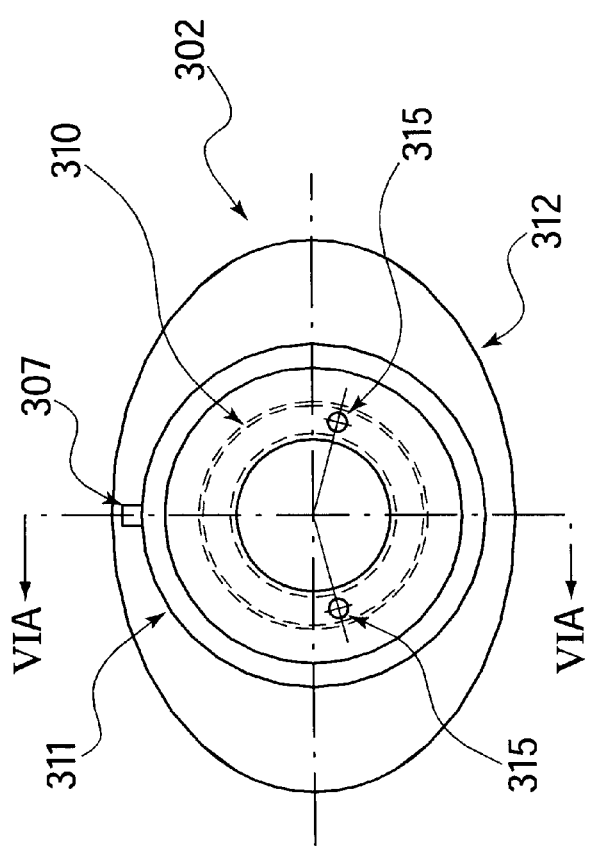
FIG. 6 is an end view of the cylinder of the embodiment of FIG. 1.

Referring now to FIGS. 6 and 6a, there is shown the cylinder 302 of plunger cap 300. The cylinder 302 includes an outer end 310 and an inner end 311. Inner end 311 is cylindrically shaped to fit snugly, but slidably, within the annular bore 322 of sleeve 301 (see FIGS. 1 and 7a). The outer end 310 may be of any convenient shape suitable for grasping by the operator, as is the collar 312 which is between the outer end 310 and the inner end 311. The ends of the beaded chains 304 can be affixed to the cylinder 302 by a snap fit, thermal bonding, pinning or any other suitable technique. In a preferred embodiment, the outer end 310 includes apertures 315 for capturing the ends of beaded chains 304, which ends of beaded chains 304 are otherwise secured in apertures 315.

Also, in the preferred embodiment, a key or pin 307 is provided in the outer surface of the inner end 311 of cylinder 302. The key 307 is adapted to be received in keyways 330, 331 in sleeve 301 to prevent allow the cylinder 302 to be locked in position when the skirt 150 is expanded, and to slide into the contracted position of the skirt 150. The key 307 operates to lock the sleeve 301 and cylinder 302 in position when the key 307 (see FIG. 7) is located in the circumferential keyway 331 and cylinder 302 is rotated relative to sleeve 301. Thus, the keyway arrangement provides a safety feature to control the movement of the cylinder 302 relative to the sleeve 301 and thereby retains the skirt 150 in the contracted position (FIGS. 4a and 5a) during insertion into the patient P. When it is desired to expand the skirt 150, the key 307 is aligned with the axial keyway 330, and the key 307 then may slide axially within keyway 330, thereby allowing cylinder 302 to slide axially relative to sleeve 301.

Figure 7:
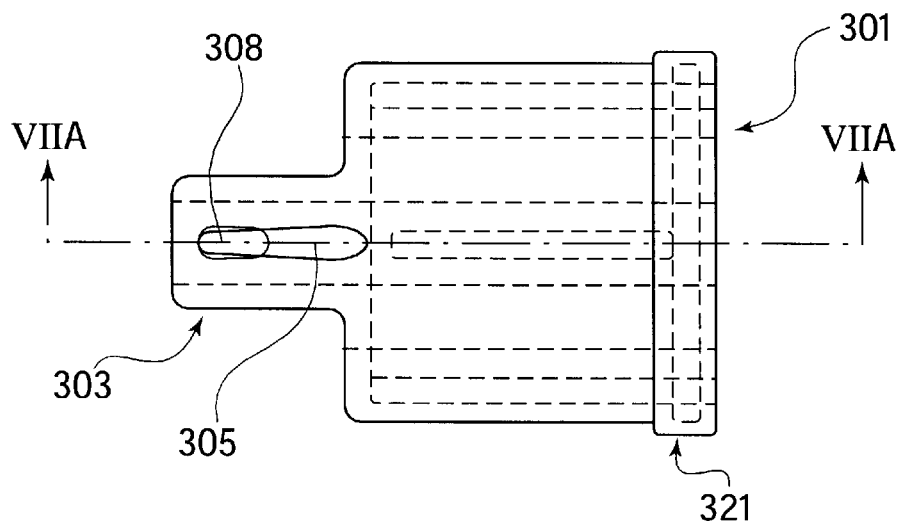
FIG. 7 is a plan view of the outer sleeve for the plunger cap shown in FIG. 1.
Figure 7A:
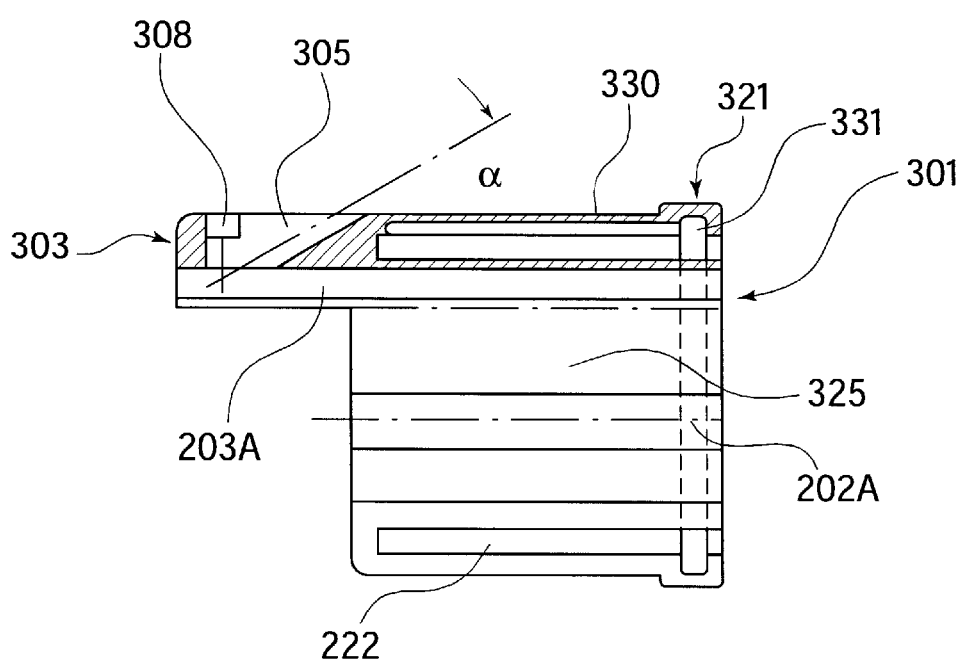
FIG. 7a is a cross-sectional elevation view of the outer sleeve, through line VIIA—VIIA of FIG. 7.

Referring concurrently to FIGS. 7 and 7a, there are shown, respectively, a plan and an elevational cross-sectional view of the sleeve 301 of plunger cap 300. The sleeve has a generally cylindrical body 301 with an optional lip 321 at one end, which lip 321 accommodates the circumferential keyway 331. The balloon tube access port 303 for the balloon tube 401 (see FIG. 1) extends from the inner end of cylinder 301 and includes a slot 305.

As seen in FIG. 7a, slot 305 in the balloon tube access port 303 may be provided to receive the balloon tube 401 which passes through the conduit 202 in tube 200, or to provide a source of pressure to inflate palate assist 800. Slot 305 may be formed at an angle α to sleeve 301.

In a preferred embodiment, an annular channel 322 is formed axially in sleeve 301. The channel 322 receives the inner end 311 of cylinder 302. The depth of the channel permits full deployment and contraction of the ring 500. The inner bore 325 of sleeve 301 is configured to receive the tube 200. Thus, the bore 325 includes the appropriate slots 202A and 203A to receive the conduits 202 and 203, respectively—which are formed in the tube 200 for the beaded chains 304, 305 and the balloon tube 401.

Referring now to FIG. 8, there is shown a plan view of one embodiment of the ring arm 508 or 509 and a portion of the connected beaded chain 304 with the control ring support 506 (or 507). The beaded chain is sufficiently long to pass through the conduit 203 in tube 200 and connect to plunger 302.

The ring arms 508, 509 are formed of a flexible plastic material. In one embodiment, a series of slits 519 are cut into the outer perimeter of the arms 508, 509. The slits 519 pass partway through the arms and permit greater flexibility, if desired. It will be readily understood that the location of the slits 519 along the length of the ring arms 508, 509, and the lack of slits in certain locations along the length of the ring arms 508, 509, allow the shape to which the expansion ring 500 contracts and expands to be varied and controlled. As shown in FIGS. 5A and 5B, the slits 519, which expand to notches 519A when the ring arms 508, 509 are expanded, are provided in both arms 508 and 509.

As shown, arms 508, 509 extend and preferably integrally interconnect with the ring tip 501. It is to be understood that in FIG. 8, two ring arms 508 and 509 would preferably be integrally molded together with a ring tip 501 and two beaded chains 304 to form a one-piece expansion ring 500 unit.

The control ring supports 506, 507 are integrally formed with the arms 508, 509 and chain 304. The supports 506, 507 are connected to the control rings 580 by stems 585. Resilient retainers 85 are looped around stems 585.

The control rings 580 are formed on the end of stems 585 of ring arms 508, 509. As described above, these rings loop around the port 133 and fit, one on top of the other, in the radiused portion 136 below the bottom of port 123. The control rings 580 slide around the port 133 to control the movement (contraction and expansion) of the ring arms 508, 509.

Referring to FIG. 8a, there is shown an elevation view of the ring arms 508, 509 and support 506, 507. The control rings 580 are joined to the supports 506, 507 by stems 585. In this view, it is seen that the ring arm 508 includes a peripheral groove 810 at one edge. In a preferred embodiment, the resilient retainer 85 takes the form of a rubber band and is looped over the support 506, 507 at stem 585.

Figure 9:
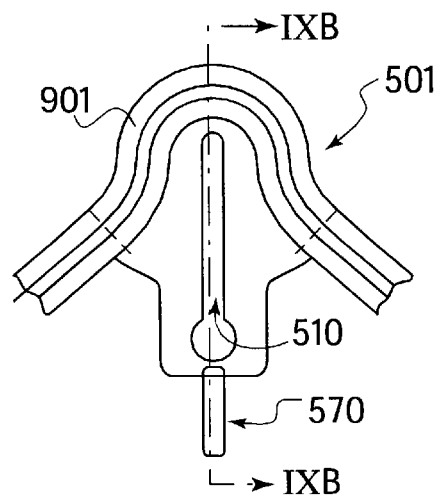
FIG. 9 is a partial plan view of the ring tip used in the embodiment shown in FIGS. 5a and 5b.
Figure 9A:
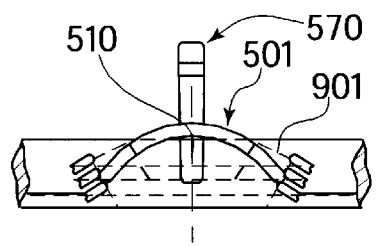
FIG. 9a is a partial elevation view of the ring tip shown in FIG. 9.
Figure 9B:
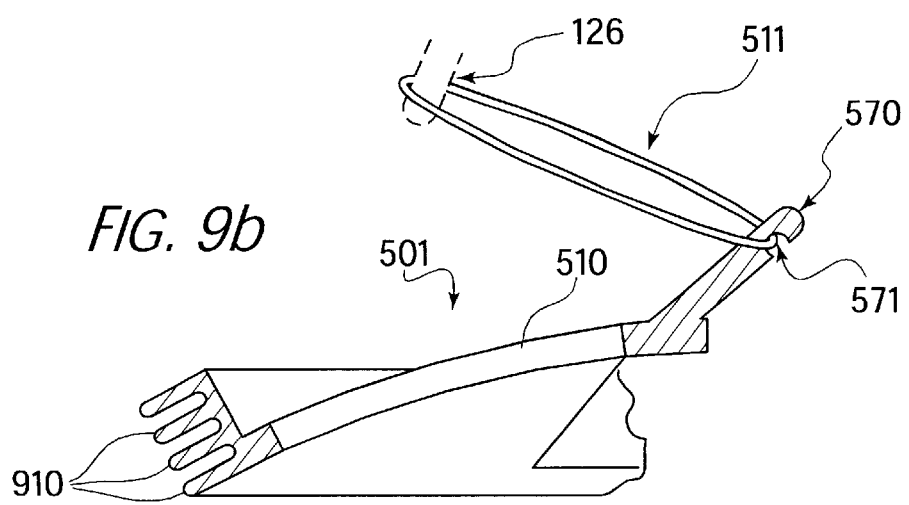
FIG. 9b is a sectional view of the ring tip taken along the lines IXB—IXB in FIG. 9.

Referring concurrently to FIGS. 9, 9a and 9b, there are shown various views of the ring tip 501 shown in FIGS. 5a and 5b. In particular, the ring tip 501 shown in FIGS. 9, 9a and 9b is preferably integrally formed with the ring arms 508 and 509 as part of a composite expansion ring 500. The curved configuration of the ring tip 501 smoothly conforms to the shape of the other portions of the mask portion 100.

FIG. 10 shows the LMA of the present invention in place in a patient, with the optional plate assist 800 contacting the hard palate H and tongue T, or the optional balloon 402 in place in the stomach S. As shown in FIG. 10, the LMA of the present invention seats properly in place in above the laryngeal opening L and epiglottis G.

FIG. 11 shows the details of a second embodiment of the mask support structure of the present invention, and in particular such a structure which includes a passage 128 for balloon 402 and balloon tube 401. In the embodiment of FIG. 11, a port 122 is formed at the upper surface of upper insert 120 and includes an aperture 127 which passes through the upper insert 120. The aperture 127 mates with the conduit 202. The port 122 allows the balloon tube 401, in the embodiment where the balloon tube 401 and balloon 402 are used, to pass through the upper insert 120. A passage 128 leads from aperture 127 to aperture 125, through which the balloon tube 401 may pass to the exterior of the mask portion 100, if the balloon tube 401 is used.

Operation of the various embodiments and methods of their use will now be described. In any embodiment which does not include the balloon 402 and balloon tube 401, the individual inserting the LMA of the present invention first contracts the skirt 150. This is accomplished by pulling out (i.e., axially outwardly) the cylinder 302 relative to the sleeve 301. Once the key 307 is aligned with the circumferential keyway 331, the cylinder 302 is rotated to thereby lock the cylinder 302 in place relative to the sleeve 301. Pulling out on the cylinder 302 pulls the beaded chains 304 outwardly, which in turn pulls non-beaded sections 304A outwardly and around pulleys 137. This movement of non-beaded sections 304A in turn pulls control rings 580 upwardly around port 133 in the direction of nose piece 501, against the bias of resilient retainers 85, which in turn pulls ring arms 508, 509 radially and axially inwardly. Movement of ring arms 508, 509 inwardly also pulls ring tip 501 radially inwardly, against the bias of spring 511. The expansion ring 500 contracts to the condition shown in FIGS. 4a and 5a.

The patient's P mouth is then opened and the LMA is inserted down the oral cavity O, with the ring tip 501 nose piece 901 facing forward. The air tube 200 is pushed inwardly into the oral cavity O until the nose piece 901 enters into the entry to the esophagus E. Once the nose piece 901 enters the esophagus E the individual inserting the LMA of the present invention will feel the nose piece 901 seating, and therefore will know that the LMA of the present invention is properly in place. Thereafter, the cylinder 302 is rotated to align key 307 with axial keyway 330, and then cylinder 302 may be released. The cylinder 301 slides axially into sleeve 301, guided by key 307 in axial keyway 330, until the skirt 150 expands sufficiently to seat against the walls of the patient's P airway. Because the key 307 is free to slide in axial keyway 330, and inner end 311 free to slide in channel 322, the expansion ring 500 and skirt 150 are free to expand to any size which is sufficient to accommodate the size of the patient's airway. The skirt 150 and expansion ring 500 therefore need not be of a specific size range to accommodate a wide range of patient P airway sizes.

Thereafter, if a palate assist 800 is part of the inserted LMA, fluid under pressure may be applied to connector 403, which fluid travels down conduit 202 and enters the interior of palate assist 800 to expand palate assist 800 until it contacts the tongue T and hard palate H, thereby securing the LMA of the present invention in place.

In one embodiment of the method of use of the present invention using the embodiment which includes balloon tube 401 and balloon 402, the above-described steps are followed. After expansion of rhe skirt 150, the balloon tube 401 and contracted balloon 402A are threaded down conduit 202, aperture 127, passage 128, aperture 125 and esophagus E until the contracted balloon 402A enters into stomach S. Fluid is then applied to connector 403, expanding balloon 402A into expanded condition 402. The expanded balloon 402 seals the stomach S off from the esophagus E, preventing gastric reflux and aspiration, and also secures the LMA of the present invention in place.

In a second embodiment of the method of use of the present invention using the embodiment which includes balloon tube 401 and balloon 402, the balloon tube 401 and contracted balloon 402A are threaded first down conduit 202, aperture 127, passage 128, and aperture 125, and then are intubated down esophagus E until the contracted balloon 402A enters into stomach S. Fluid is then applied to connector 403, expanding balloon 402A into expanded condition 402. The expanded balloon 402 seals the stomach S off from the esophagus E, preventing gastric reflux and aspiration. Next, the skirt 150 is contracted (in the same manner as described above), and the LMA of the present invention is slid down the length of balloon tube 401 (by sliding conduit 202 down the balloon tube 401), until the LMA is adjacent the mouth of the patient P. The mouth of the patient P is then opened, and the LMA of the present invention is then inserted down the patient's P oral cavity O, by continuing to slide the LMA down the balloon tube 401 until the nose piece 901 seats in the entry to the esophagus E. The skirt 150 is then expanded (in the same manner as described above); as a result, the balloon tube 401 and balloon 402 secures the LMA of the present invention in place.

Thus, there is shown and described a unique design and concept of laryngeal mask assembly. While this description is directed to a particular embodiment, it is understood that those skilled in the art may conceive modifications and/or variations to the specific embodiments shown and described herein. Any such modifications or variations which fall within the purview of this description are intended to be included as part of the invention. It is understood that the description herein is intended to be illustrative only and is not intended to be limitative. Rather, the scope of the invention described herein is limited only by the claims.

What is claimed is:

1. A laryngeal mask assembly comprising,
    a rigid support;
    a membrane attached to the rigid support;
    an expansion apparatus mounted on the rigid support adjacent to the membrane, having a first expanded position and a second contracted position, wherein when the expansion apparatus is in the first position the expansion apparatus engages and expands the membrane into its operative position, and wherein when the expansion apparatus is in the second position the expansion apparatus disengages and allows the membrane to be flaccid;
    an airway tube cooperating with the rigid support; and
    a controller for selectively moving the expansion apparatus between the first position and the second position.

2. The assembly recited in claim 1 wherein,
    the rigid support includes upper and lower support plates.

3. The assembly recited in claim 2 wherein,
    the membrane is attached to the upper and lower support plates.

4. The assembly recited in claim 2 wherein,
    the expansion apparatus is mounted between the upper and lower support plates adjacent to the membrane.

5. The assembly recited in claim 2 wherein,
    each of the upper and lower support plates include a base member and an insert member.

6. The assembly recited in claim 1 wherein,
    each base member and each insert member in each of the upper and lower support plates are attached to each other to form an integral support plate.

7. The assembly recited in claim 2, wherein the airway tube includes first and second conduits, and wherein the upper support plate includes a passageway connected to the second conduit.

8. The assembly recited in claim 1 wherein,
    the rigid support includes a port.

9. The assembly recited in claim 8 wherein,
    at least a portion of the expansion apparatus encircles the port.

10. The assembly recited in claim 9 wherein,
    the expansion apparatus includes a control ring which encircles the port.

11. The assembly recited in claim 1 wherein,
    the membrane forms a cup shape when the expansion apparatus is expanded.

12. The assembly recited in claim 1 wherein,
    the controller includes at least one elongated member attached to the expansion apparatus.

13. The assembly recited in claim 12, wherein:
    the elongated member includes a beaded chain.

14. The assembly recited in claim 12, further comprising:
    at least one pulley, the elongated member being entrained around the at least one pulley.

15. The assembly recited in claim 1, wherein:
    the expansion apparatus includes at least one ring arm.

16. The assembly recited in claim 15, wherein:
    the at least one ring arm includes a plurality of slits along a length of the ring arm.

17. The assembly recited in claim 1, wherein:
    the expansion apparatus includes a ring tip.

18. The assembly recited in claim 17, wherein:
    the ring tip includes a nose portion.

19. The assembly recited in claim 17, wherein:
    a spring biases the ring tip into an expanded condition.

20. The assembly recited in claim 1, further comprising:
    at least one biasing member biasing the expansion apparatus into an expanded condition.

21. The assembly recited in claim 1, wherein:
    the controller includes a cylinder sliding in a sleeve.

22. The assembly recited in claim 21, wherein:
    the cylinder includes a key sliding in at least one keyway in the sleeve.

23. The assembly recited in claim 1, wherein:
    the airway tube comprises a first conduit and a second conduit.

24. The assembly recited in claim 23, further comprising:
    an expandable palate assist connected to the second conduit.

25. The assembly recited in claim 23, further comprising:
    a balloon tube connected to a balloon, the balloon tube passing through the second conduit.

26. An laryngeal mask, comprising:
    a skirt;
    a support, the skirt being mounted on the support;
    an expansion ring mounted on the rigid support adjacent to the support, having a first expanded position and a second contracted position, wherein when the expansion ring is in the first position the expansion ring engages and expands the skirt into an operative stretched condition and wherein when the expansion ring is in the second position the expansion ring disengages and allows the skirt to be in an inoperative, flaccid condition;

an airway tube cooperating with the support; and a controller for selectively moving the expansion ring between the first position and the second position.

27. The laryngeal mask recited in claim 26 wherein, the support includes upper and lower support plates.

28. The assembly recited in claim 27 wherein, each of the upper and lower support plates include a base member and an insert member.

29. The assembly recited in claim 28 wherein, each base member and each insert member in each of the upper and lower support plates are attached to each other to form an integral support plate.

30. The assembly recited in claim 27, wherein:

the controller includes a cylinder sliding in a sleeve.

31. The assembly recited in claim 30, wherein:

the cylinder includes a key sliding in at least one keyway in the sleeve.

32. The laryngeal mask recited in claim 26 wherein, the skirt is attached to the upper and lower support plates.

33. The laryngeal mask recited in claim 32 wherein, the expansion ring is mounted between the upper and lower support plates adjacent to the skirt.

34. The laryngeal mask recited in claim 26 wherein, the support includes a port.

35. The laryngeal mask recited in claim 34 wherein, at least a portion of the expansion ring encircles the port.

36. The laryngeal mask recited in claim 35 wherein, the expansion ring includes a control ring which encircles the port.

37. The laryngeal mask recited in claim 26 wherein, the skirt forms a cup shape when the expansion rings is expanded.

38. The assembly recited in claim 26 wherein, the controller includes at least one elongated member attached to the expansion ring.

39. The assembly recited in claim 38, wherein:

the elongated member includes a beaded chain.

40. The assembly recited in claim 38, further comprising:

at least one pulley, the elongated member being entrained around the at least one pulley.

41. The assembly recited in claim 26, wherein:

the expansion ring includes at least one ring arm.

42. The assembly recited in claim 41, wherein:

the at least one ring arm includes a plurality of slits along a length of the ring arm.

43. The assembly recited in claim 26, wherein:

the expansion ring includes a ring tip.

44. The assembly recited in claim 43, wherein:

the ring tip includes a nose portion.

45. The assembly recited in claim 43, wherein:

a spring biases the ring tip into an expanded condition.

46. The assembly recited in claim 26, further comprising:

at least one biasing member biasing the expansion apparatus into an expanded condition.

47. The assembly recited in claim 26, wherein:

the airway tube comprises a first conduit and a second conduit.

48. The assembly recited in claim 47, further comprising:

an expandible palate assist connected to the second conduit.

49. The assembly recited in claim 47, further comprising:

a balloon tube connected to a balloon, the balloon tube passing through the second conduit.

\* \* \* \* \*

UNITED STATES PATENT AND TRADEMARK OFFICE
CERTIFICATE OF CORRECTION

PATENT NO. : 6,318,367 B1
DATED : November 20, 2001
INVENTOR(S) : Mongeon

It is certified that error appears in the above-identified patent and that said Letters Patent is hereby corrected as shown below:

Column 1,
Line 10, "an" should be -- and --

Column 2,
Line 20, "foi" should be -- for --

Column 4,
Line 37, "no," should be -- not --

Column 5,
Line 20, "ar" should be -- an --

Column 6,
Line 36, "cent al" should be -- central --

Column 7,
Line 36, "tie" should be -- the --

Column 8,
Line 62, "ale" should be -- the --

Column 14,
Line 67, "rhe" should be -- the --

Column 15,
Line 56, "cooperating with" should be -- connected to --

UNITED STATES PATENT AND TRADEMARK OFFICE
CERTIFICATE OF CORRECTION

PATENT NO. : 6,318,367 B1
DATED : November 20, 2001
INVENTOR(S) : Mongeon

It is certified that error appears in the above-identified patent and that said Letters Patent is hereby corrected as shown below:

Column 17,
Line 8, "cooperating with" should be -- connected to --

Column 18,
Line 13, "26" should be -- 28 --

Signed and Sealed this

Seventeenth Day of September, 2002

Attest:

JAMES E. ROGAN
Attesting Officer        Director of the United States Patent and Trademark Office